(12) United States Patent
Park et al.

(10) Patent No.: US 8,951,242 B2
(45) Date of Patent: Feb. 10, 2015

(54) BACTERIUM-BASED MICROROBOT INCLUDING MAGNETIC PARTICLES

(71) Applicant: Industry Foundation of Chonnam National University, Gwangju (KR)

(72) Inventors: Suk Ho Park, Gwangju (KR); Jong Oh Park, Goyang-si (KR); Sung Jun Park, Gwangju (KR)

(73) Assignee: Industry Foundation of Chonnam National University (KR)

( * ) Notice: Subject to any disclaimer, the term of this patent is extended or adjusted under 35 U.S.C. 154(b) by 0 days.

(21) Appl. No.: 13/671,769

(22) Filed: Nov. 8, 2012

(65) Prior Publication Data

US 2013/0116621 A1 May 9, 2013

(30) Foreign Application Priority Data

Nov. 8, 2011 (KR) .................. 10-2011-0115718

(51) Int. Cl.
*A61M 37/00* (2006.01)
*C12N 11/00* (2006.01)
*A61K 35/74* (2006.01)

(52) U.S. Cl.
CPC .............. *A61M 37/00* (2013.01); *C12N 11/00* (2013.01); *A61K 35/74* (2013.01)
USPC .................................. 604/891.1; 604/890.1

(58) Field of Classification Search
USPC ........ 604/131, 891.1; 435/174, 182; 424/93.4
See application file for complete search history.

(56) References Cited

U.S. PATENT DOCUMENTS 4,674,480 A * 6/1987 Lemelson ............... 424/1.25
2007/0231393 A1* 10/2007 Ritter et al. ............... 424/489

FOREIGN PATENT DOCUMENTS

| KR | 1020090122648 | 12/2009 |
|---|---|---|
| KR | 1020100048728 | 5/2010 |
| KR | 1020110093324 | 8/2011 |
| WO | WO 2010050649 A1 * | 5/2010 |

OTHER PUBLICATIONS

Behkam et al, "Characterization of Bacterial Actuation of Micro-Objects", May 2009, 2009 IEEE International Conference on Robotics and Automation, pp. 1022-1027.*
Belharet et al, "MRI-based Microrobotic system for the Propulsion and Navigation of Ferromagnetic Microparticles", Mar. 2010, Institut PRISME, pp. 1-26.*

* cited by examiner

*Primary Examiner* — Laura Bouchelle
(74) *Attorney, Agent, or Firm* — Stuart H. Mayer; Mayer & Williams PC (57) ABSTRACT

Provided is a bacterium-based microrobot, wherein bacteria are attached to a part of a surface of a microstructure including at least one or more magnetic particle, for actuating a bacterium-based microrobot more effectively.

11 Claims, 6 Drawing Sheets

BACTERIUM-BASED MICROROBOT INCLUDING MAGNETIC PARTICLES

CROSS-REFERENCE TO RELATED APPLICATION

This application claims priority to Korean Patent Application No. 10-2011-0115718 filed on Nov. 8, 2011 and all the benefits accruing therefrom under 35 U.S.C. §119, the contents of which are incorporated by reference in their entirety.

BACKGROUND

The present disclosure relates to a microrobot, and more particularly, to a bacterium-based microrobot including magnetic particles.

Development of micro/nano technologies have allowed for downsizing of structurally, functionally complex robots. But, to resolve issues on robot mobility, recognition-related sensing, and downsizing of a power source which is associated with supply of power, shape-memory alloys or electroactive polymers or the like are used as functional materials. However, the issue caused by size limitation of micro/nano robots remains a conundrum.

Actuators can be manufactured using inorganic compounds, but it is expensive to manufacture actuators, and manufacture of their components requires elaborate works. Vibrant research has been proceeding to develop actuating methods using contractile force of rat cardiac muscle cells and insect muscle cells, and motile and controllable actuators using organisms, such as bacteria having excellent motility and the like, for resolving these issues. Particularly, bacteria are also used for diagnosing and treating cancers, heart diseases, brain diseases, and so on. This means that bacteria recognize or sense diseased parts, move or actuate and treat the diseased parts. Using these, a new concept of a bacteria robot which can deliver drugs and therapeutic bacteria to diseased parts has been suggested and studied.

SUMMARY

However, for conventional bacterium-based microrobots having a form of active drug delivery which deliver a microrobot (including of a drug, a drug-encapsulated bead, and a bacterium-encapsulated bead) to lesions using the ability to recognize lesions and the ability to move of bacteria, the actual bacterial propulsion is weak, so that it is difficult to move against bloodstream when the bacterium-based robots are injected into veins. Therefore, conventional bacterium-based microrobots have been developed, postulating that bacteria that followed the blood circulation to wonder in vivo, and arrived at a lesion by chance settle down in the lesion and deliver drugs. For that reason, it takes some time to show effect, and since amounts of bacteria and drugs which finally arrive at the lesion are very small compared to the initial dosage, preferably large dosage should be administered.

The present disclosure provides a bacterium-based microrobot including magnetic particles in a microstructure, whereby the microrobot is moved by an electromagnetic field in the bloodstream and when the microrobot arrives near the lesion, active lesion-targeting can be accomplished by bacterial propulsion. However, this is for descriptive purposes only, and the scope of the present disclosure is not limited thereto.

TECHNICAL SOLUTION

In one aspect of the present disclosure, a bacterium-based microrobot comprising a microstructure comprising one or more magnetic particles, wherein the bacteria are attached to a part of the surface of the microstructure is provided.

In the bacterium-based microrobot, the magnetic particles may comprise a ferromagnetic substance, and the ferromagnetic substance may be Fe, Ni, Co, an iron oxide ($Fe_2O_3$ or $Fe_3O_4$), a ferrite ($CoFe_2O_4$, $CuFe_2O_4$, $MgFe_2O_4$, $ZnFe_2O_4$, $NiFe_2O_4$, and $MnFe_2O_4$), MnBi, MnSb, $Y_3Fe_5O_{12}$, $CrO_2$, MnAs, Gd, Dy, EuO or a ferroalloy (PePt, CoPt and the like). A diameter of the magnetic particle may be from 1 nm to 100 μm, preferably from 5 to 500 nm.

The microstructure may be in various shapes, such as a sphere, capsule, polyhedron, and the like, and its diameter may be from 1 to 1000 μm. The microstructure may have a core/shell structure, and may have a multilayer structure. In the core/shell structure, the core may be in the form of water-in-oil or oil-in-water emulsions depending on characteristics of encapsulated drugs, or in the form of a biodegradable polymer matrix in which a drug is dispersed. The shell may be prepared with a biodegradable polymer, such as hyaluronic acid (HA), alginic acid, chitosan, PLGA {poly(lactic-co-glycolic acid)}, PGA (polyglycolic acid), PLA (polylactic acid), polyhydroxyalkanoate (PHA), poly(ε-caprolactone), cellulose, meta-cellulose, carboxymethylcellulose and the like. Optionally, the core may have a multilayer structure, and an inner core of the multilayer structure may be an encapsulated magnetic particle. In this case, the inner core of the multilayer structure may be encapsulated in a magnetic particle-nondegradable polymer. It has been recently suggested that magnetic particles might cause cytotoxicity, and thus, it was lest the magnetic particle should react directly with cellular components in vivo. The drug may be an anticancer drug or a therapeutic drug for ischemic diseases or a therapeutic drug for infarction. Examples of the anticancer drug are as follows:

(i) asparaginase;
(ii) methotrexate;
(iii) pyrimidine analogs such as 5-fluorouracil, gemcitabine, and arabinosylcytosine;
(iv) hydroxy urea;
(v) purine analogs such as mercaptopurine, and thioguanine;
(vi) alkylating agents such as nitrogen mustard and cyclosporamide;
(vii) antibiotics such as anthracycline, doxorubicin, daunorubicin, idarubicin, and actinomycin D;
(viii) mitotic inhibitors such as vincristine and taxol;
(ix) antiangiogenic agents such as antibodies specific to VEGF, combretastatin A4, Fumagillin, herbimycin A, 2-methoxyestradiol, OGT 2115, TNP 470, tranilast, XRP44X, thalidomide, endostatin, salmosin, kringle domain of angiostatin, plasminogen, or apolipoprotein;
(x) intercalating agents such as carboplatin and cisplatin; and
(xi) radionuclides such as $^{18}F$, $^{90}Y$, $^{188}Re$, $^{32}P$, $^{89}Sr$, $^{165}Dy$, $^{186}Re$, $^{198}Au$, $^{153}Sm$, $^{131}I$, $^{169}Er$, $^{125}I$, $^{99}Tc$, and $^{166}Ho$.

Among the above drugs, radionuclides may be used for radiation imaging, besides radiation therapy.

Examples of the drugs for treating ischemic diseases or infarction are as follows:

A: vasodilators
(i) nitrovasodilators
examples: isosorbide dinitrate, isosorbide mononitrate, nitroglycerin, erythrityl tetranitrate, pentaerythritol tetranitrate, and sodiumnitroprusside;
(ii) angiotensin converting enzyme inhibitors
examples: benazepril, captopril, enalapril, alacepril, imidapril, perindopril, delapril, fosinopril, lisinopril, moexipril, quinapril and ramipril;

(iii) angiotensin receptor blockers examples: candersartan, eprosartan, irbesartan, olmesartan, telmisartan, valsartan and losartan;

B: cardiac depressants (i) beta blockers examples: alprenolol, bucindolol, carteolol, carvedilol, labetalol, nadolol, penbutolol, pindolol, propranolol, sotalol, timolol, acebutolol, atenolol, betaxolol, bisoprolol, esmolol, metoprolol, celiprolol, nebivolol, butaxamine, ICI-118,551, and SR 59230A;

C: analgesics (i) morphine

D: angiogenic factor examples: VEGF (vascular endothelial growth factor), Ang1 (angiopoietin 1), Ang2 (angiopoietin 2), TGF-β (transforming growth factor-β), integrin, VE-cadherin (vascular endothelial-cadherin), PA (plasminogen activator), ephrin, AC-133, PDGF (platelet-derived growth factor), MCP-1 (monocyte chemotactic protein-1), FGF (fibroblast growth factor), and PIGF (placenta growth factor).

Meanwhile, the microstructure may further comprise a drug-encapsulated bead in which a drug is encapsulated and/or a therapeutic bacterium-encapsulated bead in which a therapeutic bacterium is encapsulated, besides the magnetic particle. The drug-encapsulated bead and/or bacterium-encapsulated bead may have a core/shell structure like the microstructure of the present disclosure.

The drug is as stated above.

The bacteria may have an affinity to a tumor (U.S. Pat. No. 6,190,657 B1) or an affinity to infarcted tissues (WO 2010/137900 A1), and thereby may have the ability to target diseases, or the ability to move to the lesion and treat diseases. Absolute or facultative anaerobic bacteria may be included in such bacteria and known examples are *Salmonella, E. coli, Shigella, Bifidobacterium, Yersinia, Listeria, Mycoplasma, Streptococcus, Chlostridium*, and the like.

In addition, the bacteria may be attenuated to minimize the immune responses in vivo or may be genetically modified to express nucleic acid molecules which bind specifically to a heterologous protein or specific gene. For attenuation, msbB gene may be knocked out (U.S. Pat. No. 6,447,784 B1) or relA gene and/or spoT gene may be knocked out (WO 2010/137900 A1). The heterologous protein may be a therapeutic protein, and the therapeutic protein may be an angiogenic factor, a protein toxin, an antibody or its fragment, a tumor suppressor gene or an antiangiogenic factor. The nucleic acid molecules may be an antisense nucleotide, siRNA, shRNA, or miRNA, which bind specifically to a target gene. The target gene, that is, an object gene of which expression is intended to be inhibited, means the expression of the gene is related with occurrence and development process of a disease. For ischemic diseases, examples of such target gene include FIH-1 (Factor Inhibiting HIF) or PH2 (prolyl hydroxylase-2) and for tumors, such target gene may be an oncogene. Representative example of the oncogene includes HER2/neu. The tumor suppressor gene is able to suppress an occurrence of a tumor and representative examples include VHL (von Hippel-Lindau), APC (Adenomatous polyposis coli), CD95 (cluster of differentiation 95), ST5 (Suppression of tumorigenicity 5), YPEL3 (Yippee like 3), ST7 (Suppression of tumorigenicity 7) and ST14 (Suppression of tumorigenicity 14). The angiogenic factor is as stated above.

The gene encoding the heterologous protein or the nucleic acid molecules may be operatively linked to a promoter and transformed into bacteria, and may be inserted into a chromosome directly or be transferred in an extrachromosomal DNA, such as plasmid, BAC (bacterial artificial chromosome), fosmid, and cosmid. The promoter may be a prokaryotic promoter or a eukaryotic promoter. Prokaryotic promoters may be expressed in the bacteria and released, or may act on the lesion when bacteria are destroyed. In case that the gene is operatively connected to the eukaryotic promoter, the gene may be transferred to eukaryotic cells through bacterial phagocytosis by eukaryotic cells such as immunocytes and the like, and be expressed through gene expression system of eukaryotic cells.

Tac promoter, lac promoter, lacUV5 promoter, 1pp promoter, pLλ promoter, prλ promoter, rac5 promoter, amp promoter, recA promoter, pepT promoter, sulA promoter, T7 promoter, pBAD promoter, Tet promoter, trc promoter, SP6 promoter, T3 promoter, T5 promoter, mg1 promoter, phoA promoter, lexA promoter, uvrA promoter, uvrB promoter, uvrD promoter, umuDC promoter, cea promoter, caa promoter, recN promoter, pagC promoter, and the like may be used for the prokaryotic promoter. In addition, the promoter may be an inducible promoter to express heterologous proteins or nucleic acid molecules only when bacteria arrive at the lesion. Examples of such inducible promoter include lac promoter, lacUV5 promoter, trp promoter, tac promoter, trc promoter, rac promoter, phoA promoter, mg1 promoter, pLλ, promoter, pRλ promoter, T3 promoter, T5 promoter, T7 promoter, tet promoter, pBAD promoter and SP6 promoter.

In addition, the bacteria may further include a reporter gene which is operatively connected to the promoter, for diagnosing diseases and monitoring the extent of treatment. Examples of the reporter gene may be luminescent proteins, fluorescent proteins, reporter proteins for positron emission tomography, avidin, or genes encoding a receptor. Examples of the luminescent proteins include firefly luciferase, *Renilla* luciferase, *Metridia* luciferase, and the like. Examples of the fluorescent proteins include GFP (green fluorescent protein), YFP (yellow fluorescent protein), RFP (red fluorescent protein), OFP (orange fluorescent protein), CFP (cyan fluorescent protein), BFP (blue fluorescent protein), far-red fluorescent protein or tetracystein motif. Examples of the receptor proteins include dopamine receptor, somatostatin receptor, sodium-iodide transporter, transferrin receptor, ferritin, and an iron transporter (magA).

The bacteria may have directionality by being attached selectively to a part of a surface of the microstructure. This is possible by selectively controlling surface energy of the part of the surface of the microstructure. For example, when the surface of one hemisphere of the spherical microstructure of hydrophobic material is modified to be hydrophilic, bacteria are attached selectively to the hydrophobic hemisphere side rather than to the hydrophilic hemisphere. On the contrary, when a certain hemisphere of the microstructure of hydrophilic material is selectively coated with a hydrophobic material, such as carbon nanotubes, bacteria are attached selectively to a hydrophobic material-coated hemisphere side.

The surface may be modified with plasma treatment and the plasma-treated surface may be hydrophilic or hydrophobic depending on the characteristic of plasma-treated gas. For example, when air is converted to plasma by a corona discharge and the like, the surface is modified to be hydrophilic by hydroxyl groups, and also when atmospheric plasma is generated by inert gas such as Ar, He, and the like, hydroxyl groups are formed by $O_2/H_2$ in the air and the surface is modified to be hydrophilic. On the other hand, using fluorine-based gas such as $CF_4$ or carbon-based gas such as $CH_4$ generates large amounts of hydrophobic groups, and the surface is modified to be hydrophobic. Hydrophilic or hydrophobic modification may be controlled depending on the characteristic of a first adsorptive object. For example, since bacteria prefer hydrophobic surfaces, adsorption of bacteria onto a certain area may be blocked through hydrophilic surface modification. In addition, it is possible to produce a surface modified with amine groups by generating plasma with ammonia gas, and in this case, it is possible not only to suppress the adsorption of hydrophobic materials, but also to covalently attach materials having a carboxyl group (COOH), for example, proteins or peptides, selectively to the certain surface area of the microstructure. As one embodiment, when the surface is modified to have amine groups on the certain surface area by generating plasma with ammonia, bacteria as a first adsorptive object may be attached selectively to the side unmodified with amine groups, and specific antibodies to cancer antigens as a second adsorptive object may be connected covalently to the side modified with amine groups.

A method of modifying selectively only a certain surface of a microstructure, in which it is difficult to modify selectively only a part of a surface, such as spherical or capsule-type microstructures is illustrated by example as follows:

Using a difference in specific gravity between a microstructure and a hydrogel, only a part of the microstructure is allowed to submerge in the hydrogel, and a polymer such as PDMS (polydimethyl siloxane) is spread and hardened on the hydrogel in which the microstructure is partly submerged, and then, when separating the hydrogel and the polymer, the hydrogel can be separated from the polymer with the microstructure being fixed. To the surface of the microstructure exposed to the polymer surface, plasma may be treated, or an adsorbent (hydrophobic materials, such as tetrafluoropolyethylene and carbon nanotubes) or absorption inhibitor (hydrophilic materials, such as BSA, polyamines, polyols, and the like) may be spread. The microstructure of which a certain surface is modified can be obtained by separating the microstructure from the polymer using ultrasonic waves and the like, after treating plasma or fixing the adsorbent or absorption inhibitor. The surface area of the modified surface can be controlled by regulating the hydrogel concentration. For example, when increasing the hydrogel concentration, the microstructure is less submerged in the hydrogel, and in case that this microstructure is transferred on the polymer, the exposed area also is reduced. In this case, when a small area is made to be hydrophilic by plasma treatment, the area to which bacteria are attached is increased contrariwise. Then, the propulsive force may be increased due to the attachment of many bacteria, but since the directionality is reduced, the vector sum of the propulsive force may be reduced, instead. On the contrary, when decreasing the hydrogel concentration, the microstructure is submerged deeply, and in case that this microstructure is transferred on the polymer, the exposed area also is increased. In this case, when providing hydrophilicity to a large area by oxygen plasma treatment, bacteria can attach to a small certain surface contrariwise. Then, directionality is increased, but the propulsive force may be reduced because the absolute number of attached bacteria is insufficient.

In accordance with another aspect of the present disclosure, provided is an electromagnetic actuating bacterium-based microrobot system, including an EMA (electromagnetic actuation) actuating system including an EMA coil system and a location recognition module for recognizing a location of a microrobot; an integral control module for controlling the EMA actuating system; and the bacterium-based microrobot, which can enter a living body and deliver a drug and therapeutic bacteria. The microrobot actuating system including an EMA coil system is disclosed in detail in Korea Patent Publication Number 2010-0136206, Korea Patent Publication Number 2010-0104506, Korea Patent Publication Number 2011-0000779, and Korea Patent Number 1001291, and the like. The above patent documents are entirely incorporated herein by reference.

In the electromagnetic actuating bacterium-based microrobot system, the location recognition module may be a bidirectional X-ray or MRI system.

According to one embodiment of the present disclosure, it is possible to actualize the bacterium-based microrobot including magnetic particles which can deliver therapeutic drugs and/or bacteria to the lesion effectively in a living body with a smaller dosage. Of course, the scope of the present disclosure is not limited to this effect.

BRIEF DESCRIPTION OF THE DRAWINGS

Exemplary embodiments can be understood in more detail from the following description taken in conjunction with the accompanying drawings, in which.

DETAILED DESCRIPTION OF EMBODIMENTS

Hereinafter, specific embodiments will be described in detail with reference to the accompanying drawings. However, the present disclosure is not limited to embodiments disclosed in the following and can be realized in different and various forms. The following embodiments are provided for complete disclosure of the present invention and complete enlightenment about the category of the present invention for those skilled in the art. In addition, sizes of components can be enlarged or reduced in drawings for the sake of convenient explanation.

Figure 1:
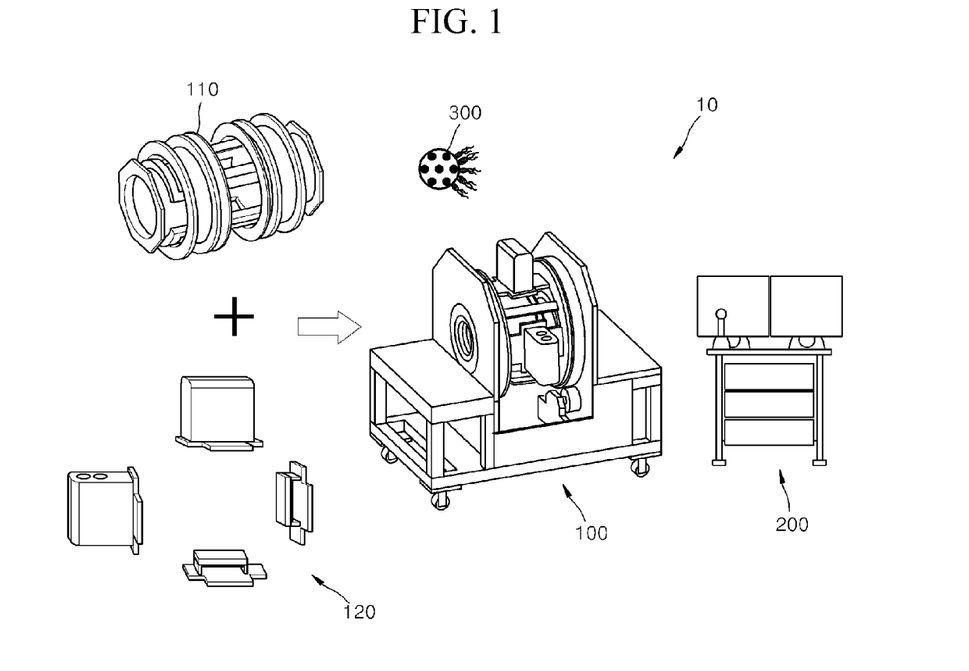
FIG. 1 is a schematic diagram showing the electromagnetic actuating bacterium-based microrobot system in accordance with an exemplary embodiment of the present disclosure.

FIG. 1 is a schematic diagram showing the electromagnetic actuating bacterium-based microrobot system 10 in accordance with an exemplary embodiment of the present disclosure. First, the EMA (electromagnetic actuation) coil system 110 exists for electromagnetic actuation and the location recognition module 120 exists for recognizing a location of the microrobot 300. The EMA actuating system 100 in which the coil system 110 and the location recognition module 120 are combined exists and the integral controller 200 for controlling the EMA actuating system exists. Finally, the bacterium-based microrobot 200 which can deliver drugs and therapeutic bacteria in vivo exists. The electromagnetic actuating bacterium-based microrobot system 10 comprises the above mentioned constitution.

Figure 2:
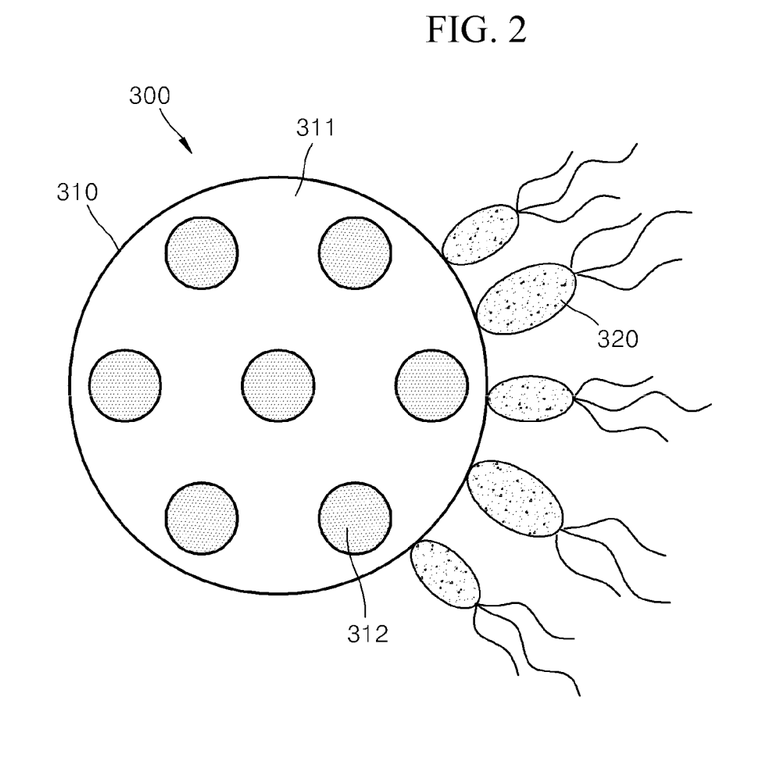
FIG. 2 is a schematic conceptual diagram of the bacterium-based microrobot in accordance with a first embodiment of the present disclosure.

FIG. 2 is a schematic conceptual diagram of the bacterium-based microrobot 300 in accordance with a first embodiment of the present disclosure. In accordance with one embodiment of the present disclosure, the bacterium-based microrobot 300 comprises the microstructure 310 and bacteria 320 which are attached to the surface of the microstructure. In accordance with one embodiment of the present disclosure, the microstructure 310 has a core/shell structure and the inside core includes one or more magnetic particles 312 dispersed in a first drug 311. In this constitution, the bacterium-based microrobot 300 is moved near the lesion of interest using the electromagnetic actuating bacterium-based microrobot system 10 illustrated in FIG. 1 and closely to the lesion using the ability to recognize and move of bacteria 320. Finally, treatment is carried out by releasing the drug from the bacterium-based microrobot 300 and delivering it to the lesion.

Figure 3:
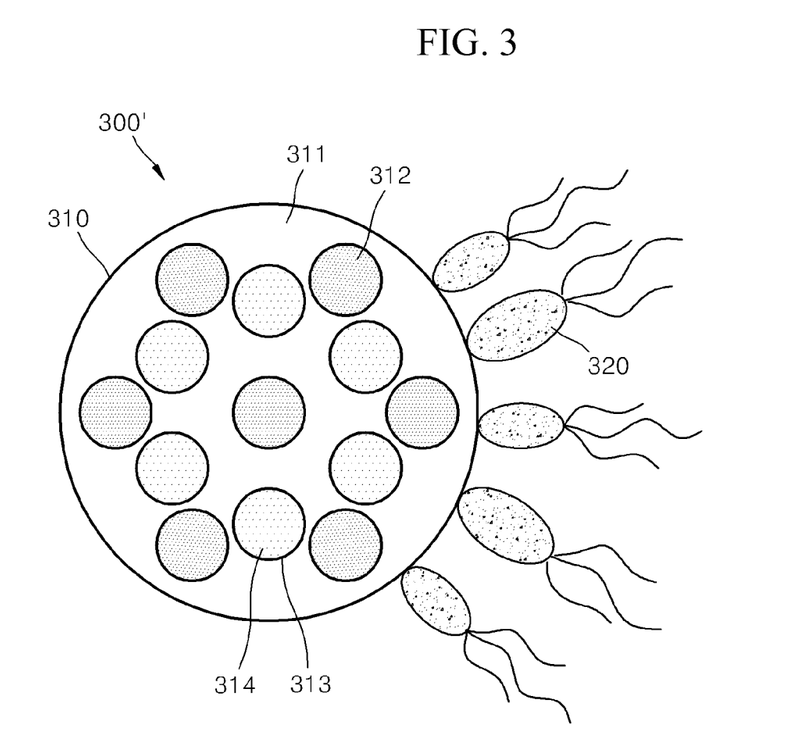
FIG. 3 is a schematic conceptual diagram of the bacterium-based microrobot in accordance with a second embodiment of the present disclosure.

FIG. 3 is a schematic conceptual diagram of the bacterium-based microrobot 300' in accordance with a second embodiment of the present disclosure. In accordance with the embodiment, the bacterium-based microrobot is in the form in which the microstructure 310 further comprises the drug-encapsulated bead 313. The rest constitution or actuating method is identical with the bacterium-based microrobot shown in FIG. 2 and the difference is that it has an advantage of being capable of delivering one or more second drugs 314 which are encapsulated in the drug-encapsulated bead 313 to the lesion, in addition to the first drug 311. The first drug 311 and the second drug 314 may be in a same or different category. The first drug 311 and the second drug 314 may be in a different category and cause synergism. In case that drug efficacy is decreased by the interaction between the first and the second drugs, the shell may be used as a barrier to block the interaction between the drugs to maximize drug efficacy.

Furthermore, the first drug 311 may be a prodrug-activating agent or enzyme to convert the state of the second drug 314 from prodrug to activated drug. Conversely, the second drug 314 may be a prodrug-activating agent or activating enzyme to convert state of the first drug 311 from prodrug to activated drug.

Figure 4:
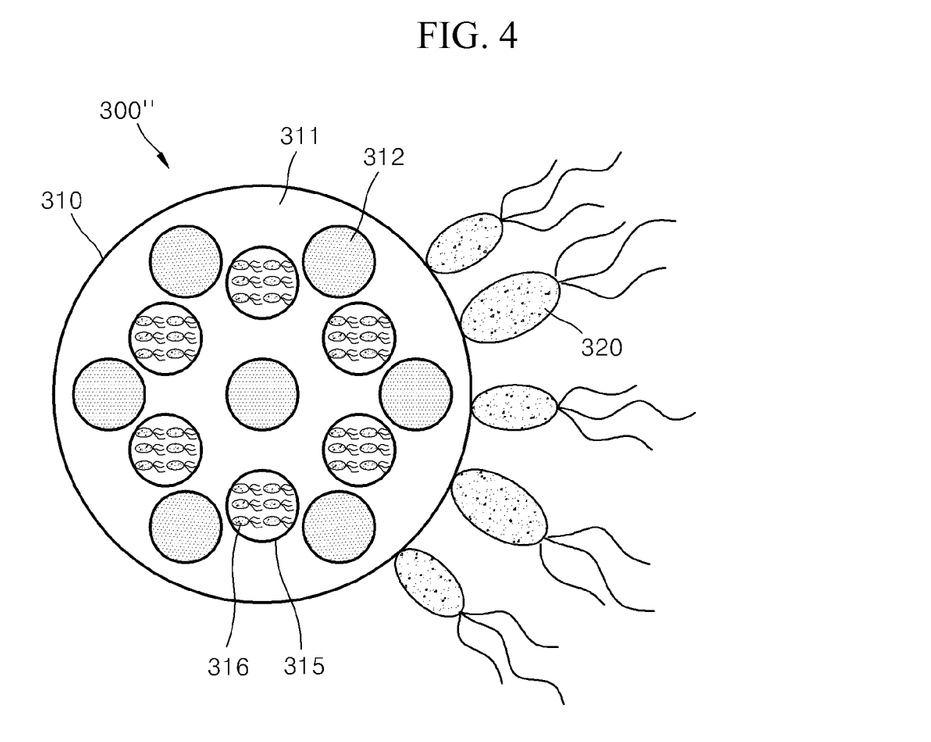
FIG. 4 is a schematic conceptual diagram of the bacterium-based microrobot in accordance with a third embodiment of the present disclosure.

FIG. 4 is a schematic conceptual diagram of the bacterium-based microrobot 300" in accordance with a third embodiment of the present disclosure. The embodiment is in the form in which the microstructure 310 further comprises the therapeutic bacteria-encapsulated bead 315 in the bacterium-based microrobot. In the therapeutic bacteria-encapsulated bead 315, therapeutic bacteria 316 are encapsulated. The bacteria 312 and the therapeutic bacteria 316 may be same or different strains. The bacteria 312 may be strengthen the motility and/or the ability to target diseases and the therapeutic bacteria 316 may be genetically modified to strengthen the ability to treat diseases, express therapeutic proteins, or produce therapeutic drugs by metabolism. The rest constitution or actuating method is identical with the first embodiment and the difference is that it is capable of delivering the therapeutic bacteria 316 which are encapsulated in the therapeutic bacteria-encapsulated bead 315 to the lesion, in addition to the first drug 311. It has an advantage of capable of diagnosing or treating the lesion by delivering the therapeutic bacteria 316 additionally.

Figure 5:
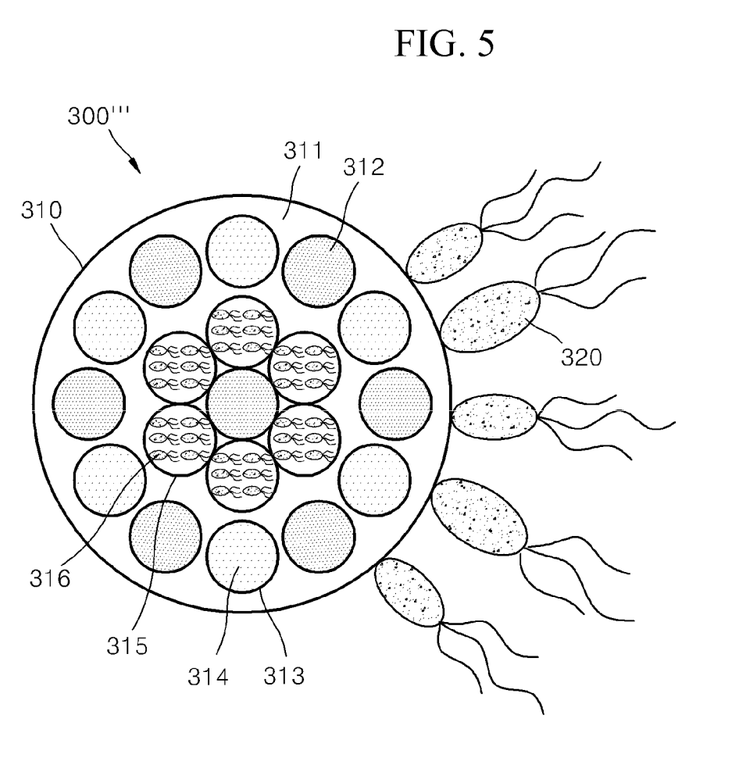
FIG. 5 is a schematic conceptual diagram of the bacterium-based microrobot in accordance with a fourth embodiment of the present disclosure.

FIG. 5 is a schematic conceptual diagram of the bacterium-based microrobot 300''' in accordance with a fourth embodiment of the present disclosure. In the bacterium-based microrobot in accordance with the first embodiment, the bacterium-based microrobot further comprises one or more drug-encapsulated beads 313 and one or more therapeutic bacteria-encapsulated beads 315 respectively. The rest constitution or actuating method is identical with the first embodiment and the difference is that it is capable of delivering the second drug 314 which is encapsulated in the drug-encapsulated bead 313 and the therapeutic bacteria 316 which are encapsulated in the therapeutic bacteria-encapsulated bead 315 to the lesion, in addition to the first drug 311. It has an advantage of capable of treating diseases with drugs or diagnosing or treating the lesion with bacteria by delivering the second drug 314 and the therapeutic bacteria 316 additionally.

Figure 6:
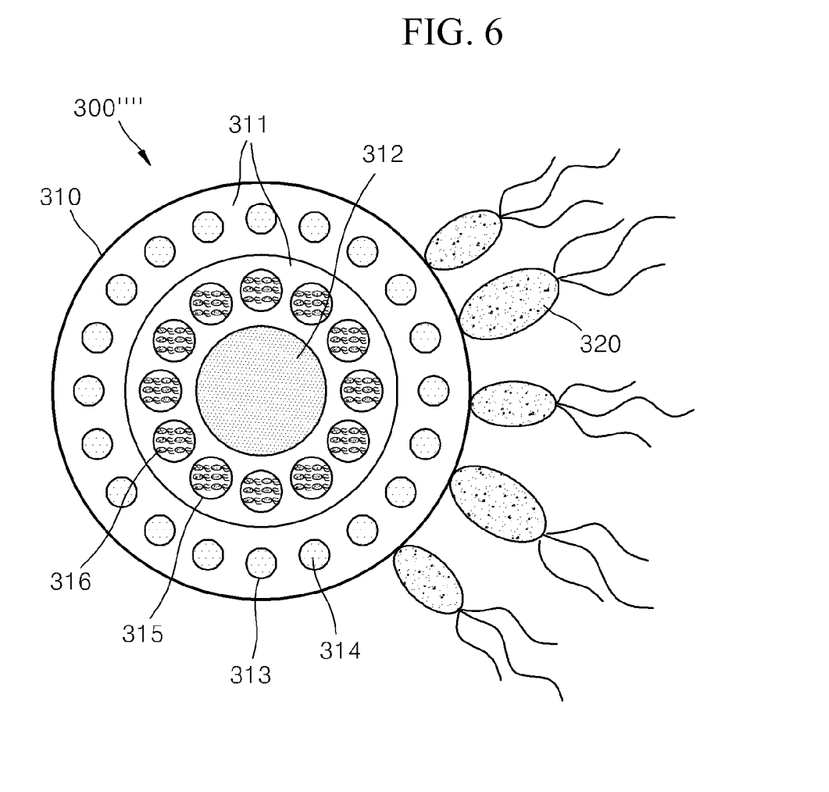
FIG. 6 is a schematic conceptual diagram of the bacterium-based microrobot in accordance with a fifth embodiment of the present disclosure.

FIG. 6 is a schematic conceptual diagram of the bacterium-based microrobot 300'''' in accordance with a fifth embodiment of the present disclosure. The bacterium-based microrobot 300'''' in accordance with the fifth embodiment has the microstructure 310 of multilayer structure. Magnetic particles 312 may be dispersed in at least one or more layer of the multilayer structure microstructure and the first drug 311 may be dispersed in other layer. The first drug 311 may exist in emulsion type or be encapsulated as the second drug 314 in the drug-encapsulated bead 313. Additionally, the therapeutic bacteria 316 which are encapsulated in the therapeutic bacteria-encapsulated bead 314 may be included.

Although the bacterium-based microrobot including magnetic particles has been described with reference to the specific embodiments shown in drawings, it is just for illustrative purposes. It will be readily understood by those skilled in the art that various modifications and equivalent other embodiments are possible. Therefore, the true scope of technical protection of the present disclosure should be defined by the technical ideas of appended claims.

DESCRIPTION OF NUMERICAL SYMBOLS
FOR MAJOR PARTS OF DRAWINGS

10: electromagnetic actuating bacterium-based microrobot system
100: EMA (electromagnetic actuation) actuating system
110: EMA (electromagnetic actuation) coil system
120: location recognition module
200: integral controller
300, 300', 300'', 300''', 300'''': bacterium-based microrobot
310: microstructure
320: bacteria
311: first drug
312: magnetic particles
313: drug-encapsulated bead
314: second drug
315: therapeutic bacteria-encapsulated bead
316: therapeutic bacteria

What is claimed is:

1. A bacterium-based microrobot comprising a microstructure having core/shell structure consisting of a core containing a drug and a shell comprising biodegradable polymer enclosing the core, wherein one or more magnetic particles having diameter of 5 to 500 nm are dispersed in the core and wherein the bacteria are selectively attached to a hydrophobic hemispherical part of the surface of the microstructure, by modifying a hemispherical surface of the microstructure to be hydrophilic if the surface of the microstructure is hydrophobic or modifying the hemispherical surface of the microstructure to be hydrophobic if the surface of the microstructure is hydrophilic.

2. The bacterium-based microrobot of claim 1, wherein the magnetic particles comprise a ferromagnetic substance.

3. The bacterium-based microrobot of claim 1, wherein the microstructure has a multilayer structure.

4. The bacterium-based microrobot of claim 1, further comprising a drug-encapsulated bead in which a drug is encapsulated.

5. The bacterium-based microrobot of claim 4, wherein the drug is an anticancer drug, a radionuclide, a therapeutic drug for ischemic diseases, or a therapeutic drug for infarction.

6. The bacterium-based microrobot of claim 4, further comprising a therapeutic bacterium-encapsulated bead in which therapeutic bacteria are encapsulated.

7. The bacterium-based microrobot of claim 4, wherein the drug is an anticancer drug, a radionuclide, a therapeutic drug for ischemic diseases, or a therapeutic drug for infarction.

8. The bacterium-based microrobot of claim 1, further comprising a therapeutic bacterium-encapsulated bead in which therapeutic bacteria are encapsulated.

9. The bacterium-based microrobot of claim 1, wherein the bacteria are selectively attached to the hydrophobic hemispherical surface of the microstructure by controlling surface energy of a hemispherical surface of the microstructure.

10. An electromagnetic actuating bacterium-based microrobot system, comprising:
   an EMA (electromagnetic actuation) actuating system comprising an EMA coil system and a location recognition module for recognizing a location of a microrobot;
   an integral control module for controlling the EMA actuating system; and
   the bacterium-based microrobot of claim 1 capable of delivering a drug and therapeutic bacteria in vivo.

11. The electromagnetic actuating bacterium-based microrobot system of claim 10, wherein the location recognition module is a bidirectional X-ray or MRI system.

* * * * *